United States Patent
Mach et al.

(10) Patent No.: US 8,506,927 B2
(45) Date of Patent: Aug. 13, 2013

(54) PEGYLATED FLUOROBENZAMIDE ANALOGUES, THEIR SYNTHESIS AND USE IN DIAGNOSTIC IMAGING

(75) Inventors: Robert H. Mach, Eureka, MO (US); Zhude Tu, Frontenac, MO (US)

(73) Assignee: Washington University, Saint Louis, MO (US)

(*) Notice: Subject to any disclaimer, the term of this patent is extended or adjusted under 35 U.S.C. 154(b) by 99 days.

(21) Appl. No.: 13/344,084

(22) Filed: Jan. 5, 2012

(65) Prior Publication Data
US 2012/0171119 A1 Jul. 5, 2012

Related U.S. Application Data

(60) Provisional application No. 61/429,758, filed on Jan. 5, 2011.

(51) Int. Cl.
*A61K 51/00* (2006.01)
*A61M 36/14* (2006.01)

(52) U.S. Cl.
USPC .................. 424/1.11; 424/1.85; 424/1.89

(58) Field of Classification Search
USPC ...................... 424/1.11, 1.85, 1.89
See application file for complete search history.

(56) References Cited

U.S. PATENT DOCUMENTS

| 7,390,902 | B2 | 6/2008 | Mach et al. | |
| 7,659,400 | B2 | 2/2010 | Mach et al. | |
| 7,947,838 | B2 * | 5/2011 | Mach et al. | 546/86 |

OTHER PUBLICATIONS

Bowen WD, Bertha CM, Vilner BJ, Rice KC. CB-64D and CB-184: ligands with high sigma 2 receptro affinity and subtype selectivity. Eur. J. Pharmacol. May 1995;278(3):257-260.
Kassiou M, Dannals RF, Liu X, Wong DF, Ravert HT, Scheffel UA. Synthesis and in vivo evaluation of a new PET radioligand for studying sigma-2 receptors. Bioorg Med Chem. Jun. 2005;13(11):3623-3626.
Berardi F, Ferorelli S, Abate C, Colabufo NA, Contino M, Perrone R, Tortorella V. 4-(tetralin-1-yl)- and 4-(naphthalen-1-yl)alkyl derivatives of 1-cyclohexylpiperazine as sigma receptor ligands with agonist sigma2 activity. J. Med. Chem. Apr. 2004;47(9):2308-2317.
Mach RH, Huang Y, Freeman RA, Wu L, Blair S, Luedtke RR. Synthesis of 2-(5-bromo-2,3-dimethoxyphenyl)-5-(aminomethyl)-1H-pyrrole analogues and their binding affinities for dopamine D2, D3, and D4 receptors. Bioorg. Med. Chem. Jan. 2003;11(2):225-233.
Huang Y, Hammond PS, Wu L, Mach RH. Synthesis and structure-activity relationships of N-(1-benzylpiperidin-4-yl) arylacetamide analogues as potent sigma1 receptor ligands. J. Med. Chem. Dec. 2001;44(25):4404-15.
Tu Z, Dence CS, Ponde DE, Jones L, Wheeler KT, Welch MJ, Mach RH. Carbon-11 labeled sigma2 receptor ligands for imaging breast cancer. Nucl. Med. Biol. Jul. 2005;32(5):423-430.
Xu J, Tu Z, Jones LA, Vangveravong S, Wheeler KT, Mach RH. [3H]N-[4-(3,4-dihydro-6,7-dimethoxyisoquinolin-2(1H)-yl)butyl]-2-methoxy-5-methylbenzamide: a novel sigma-2 receptor probe. Eur. J. Pharmacol. Nov. 2005; 525(1-3):8-17.
Hou C, Tu Z, Mach R, Kung HF, Kung MP. Characterization of a novel iodinated sigma-2 receptor ligand as a cell proliferation marker. Nucl. Med. Biol. Feb. 2006;33(2):203-9.
Mach RH, Huang Y, Buchheimer N, Kuhner R, Wu L, Morton TE, Wang L, Ehrenkaufer RL, Wallen CA, Wheeler KT. [[(18)F]N-(4'-fluorobenzyl)-4-(3-bromophenyl) acetamide for imaging the sigma receptor status of tumors: comparison with [(18)F]FDG, and [(125)I]IUDR. Nucl Med Biol. May 2001;28(4):451-458.
Colabufo NA, Berardi F, Contino M, Fazio F, Matarrese M, Moresco RM, Niso M, Perrone R, Tortorella V. J. Distribution of sigma receptors in EMT-6 cells: preliminary biological evaluation of PB167 and potential for in-vivo PET. J. Pharm Pharmacol. Nov. 2005;57(11):1453-1459.
Bonhaus DW, Loury DN, Jakeman LB, to Z, DeSouza A, Eglen RM, Wong EH. [3H]BIMU-1, a 5-hydroxytryptamine3 receptor ligand in NG-108 cells, selectively labels sigma-2 binding sites in guinea pig hippocampus. J. Pharmacol. Exp. Ther. Nov. 1993;267(2):961-970.

* cited by examiner

*Primary Examiner* — Michael G Hartley
*Assistant Examiner* — Melissa Perreira
(74) *Attorney, Agent, or Firm* — Zackson Law LLC; Saul L. Zackson (57) ABSTRACT

Pegylated fluoroalkoxybenzamide compounds which selectively bind Sigma-2 receptors are disclosed. These compounds, when labeled with a positron-emitting radioisotope such as $^{18}F$, can be used as radiotracers for medical imaging such as imaging of tumors by positron emission tomography (PET). In addition, these compounds, when labeled with $^{123}I$, can be used as radiotracers for imaging of tumors by single photon emission computed tomography (SPECT). Methods for synthesis of these compounds are also disclosed.

20 Claims, 2 Drawing Sheets

PEGYLATED FLUOROBENZAMIDE ANALOGUES, THEIR SYNTHESIS AND USE IN DIAGNOSTIC IMAGING

CROSS-REFERENCE TO RELATED APPLICATIONS

This application claims the benefit of priority of U.S. Provisional Application Ser. No. 61/429,758, filed Jan. 5, 2011, which is incorporated herein by reference in its entirety.

INTRODUCTION

Sigma receptors are a class of receptors that are expressed in many normal tissues, including liver, kidneys, endocrine glands, and the central nervous system (CNS) (Walker, J. M., et al. Pharmacol Rev 42: 355-402 1990). It has been well established that there are at least two types of sigma receptors, sigma-1 ($\sigma_1$) and sigma-2 ($\sigma_2$) (Walker, J. M., et al. Pharmacol Rev 42, 355-402, 1990). Overexpression of $\sigma_2$ receptors has been reported in a variety of human and murine tumors (Bem, W. T., et al., Cancer Res 51: 6558-6562, 1991; Vilner, B. J., et al., In: Multiple sigma and PCP receptor ligands: mechanisms for neuromodulation and neuroprotection?, Kamenka, J. M., and Domino, E. F., ed, Ann Arbor (Mich.), 7 NPP Books, p. 341-353, 1992; Mach, R. H., et al., Cancer Res. 57: 156-161, 1997).

Figure 1:
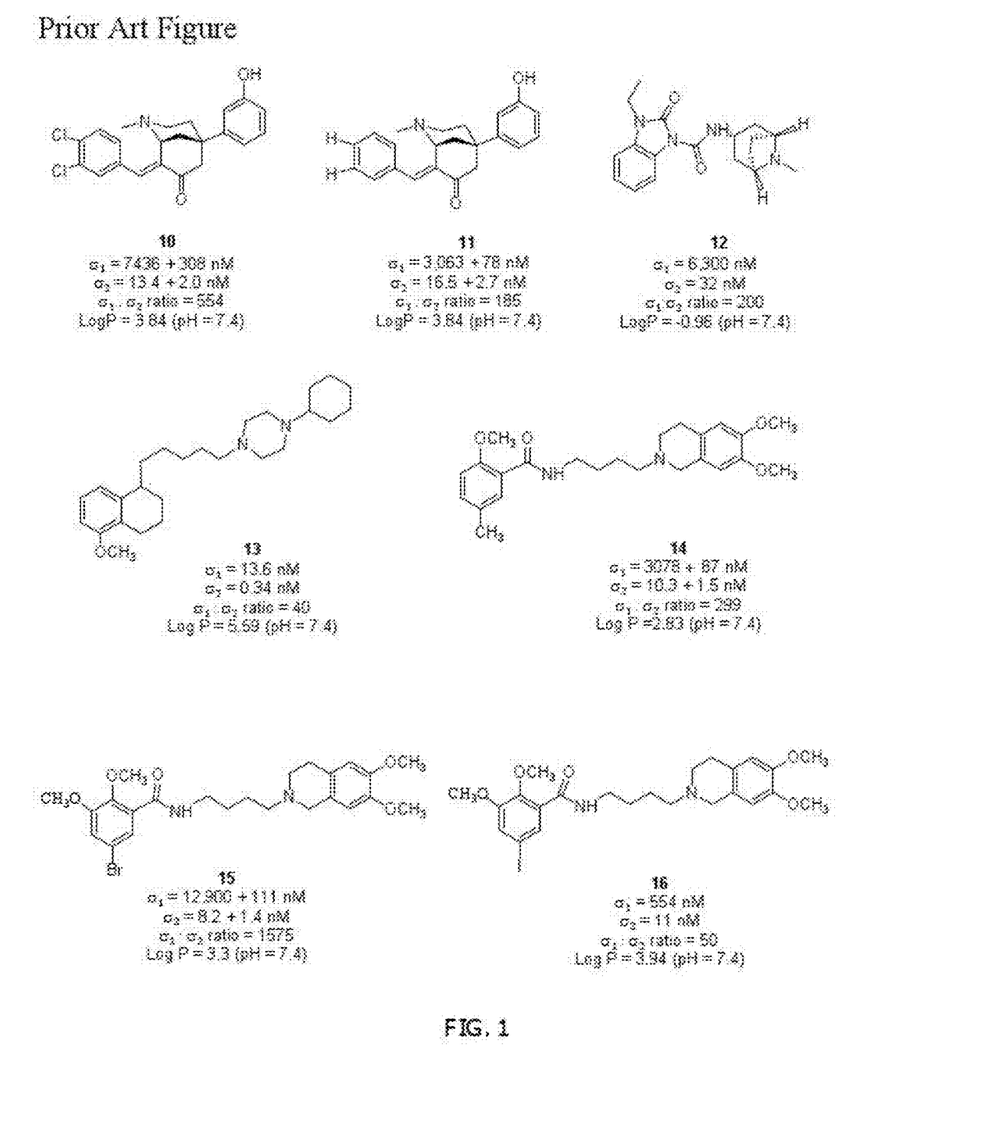
FIG. 1 illustrates prior art compounds.

Searches for $\sigma_2$ selective ligands has led to the identification of a number compounds having modest to high selectivity for $\sigma_2$ versus $\sigma_1$ receptors. As set forth in FIG. 1, these compounds include CB-184 (10), CB-64D (11), BIMU-1 (12) (Bowen, W. D., et al., Eur. J. Pharmacol. 278: 257-260, 1995; Bonhaus, D. W., et al., J. Pharmacol. Exp. Ther. 267: 961-70, 1993). and PB-167 (13) (Colabufo, N. A., et al., J. Pharm. Pharmacol. 57: 1453-1459, 2005; Kassiou, M., et al., Bioorg. Med. Chem. 13: 3623-3626, 2005; Berardi, F., et al., J. Med. Chem. 2004, 47: 2308-2317) as well as certain benzamide analogs (14-16) (Mach, R. H., et al., Bioorg. Med. Chem. 11: 225-233, 2003; Huang, Y., et al., J. Med. Chem. 44: 4404-15, 2001; U.S. patent application Ser. No. 10/903,771 to Mach et al). We previously reported the evaluation of several $^{11}$C, $^{76}$Br and $^{125/123}$I radiolabelled conformationally-flexible benzamide analogs using EMT-6 tumor-bearing female Balb/c mice (Tu, Z., et al., Nucl. Med. Biol. 32: 423-430, 2005; Xu, J., et al., Eur. J. Pharmacol. 525 (1-3): 8-17, 2005; Hou, C., et al., Nucl. Med. Biol. February, 33: 203-9, 2006). Initial in vivo studies of 5-methyl-2-[$^{11}$C]-methoxy-N-[2-(6,7-dimethoxy-3,4-dihydro-1H-isoquinolin-2-yl)-butyl]-benzamide and 5-[$^{76}$Br]-bromo-2,3-dimethoxy-N-[2-(6,7-dimethoxy-3,4-dihydro-1H-isoquinolin-2-yl)-butyl]-benzamide indicated that these compounds were potential radiopharmaceuticals for imaging solid tumors and their proliferative status with positron emission tomography (PET). However, the radionuclide properties of $^{76}$Br and $^{11}$C make these isotopes less than ideal for PET imaging. For example, images produced by PET using $^{76}$Br as a radiotracer are often blurry, (Laforest, R., et al., IEEE Transactions on Nuclear Science, 49: 2119-2126, 2002), and the short half-life of $^{11}$C ($t_{1/2}$=20.4 min) places time constraints on tracer synthesis and duration of scan sessions. Contrast between tumor and normal tissues can be less than satisfactory when a $\sigma_2$-selective radiotracer tagged with $^{11}$C is used in PET imaging.

U.S. Pat. No. 7,659,400 to Mach et al., discloses compounds and salts thereof of structure wherein m is an integer from 1 to about 10, n is an integer from 1 to about 10, and $R_1$ and $R_2$ are each independently selected from the group consisting of H, a halogen selected from the group consisting of I, Br, Cl and F, a $C_{1-4}$ alkoxy, a $C_{1-4}$ alkyl, a $C_{1-4}$ fluoroalkyl, a $C_{1-4}$ fluoroaloxy, $CF_3$, $OCF_3$, $SCH_3$, $SCF_3$, and $NH_2$. In some embodiments, the F can be an $^{18}$F. In some embodiments, $R_1$ or $R_2$ can be an iodine (I), which can be an $^{123}$I. However, some of these compounds may not have the solubility, clearance rate, toxicity or stability that may be desirable for some uses. Accordingly, alternative $\sigma_2$-selective ligands that can be used as radiotracers in PET imaging are needed.

SUMMARY

The present inventors have developed a series of compounds. In some embodiments, a radiolabeled compound or salt thereof disclosed herein can be used as a tracer for diagnostic imaging, such as diagnostic imaging of tumors. In various configurations, a compound or salt thereof disclosed herein can be used as a tracer in imaging methods such as positron emission tomography (PET) or single photon emission computed tomography (SPECT). In various embodiments, a compound or salt thereof of the present teachings can selectively bind Sigma receptors, and in particular can bind Sigma-2 receptors in preference to Sigma-1 receptors. In various embodiments, the compounds and salts thereof can also selectively bind to tumor cells, and thus can also be used as tracers for detecting tumor cells. In some embodiments, a compound or salt thereof can comprise a positron-emitting radioisotope such $^{11}$C, $^{13}$N, $^{15}$O, $^{18}$F, $^{76}$Br or $^{124}$I. In various configurations, such compounds and salts thereof can be used as radiotracers for imaging biological tissue such as tumors using SPECT. In some embodiments, a compound or salt thereof can comprise a gamma ($\gamma$)-emitting radioisotope such as $^{123}$I.

In some embodiments, a compound of the present teachings is a pegylated fluoroalkoxybenzamide compound or a salt thereof having a structure wherein m is an integer from 2 to 5, n is an integer from 1 to about 10, and $X_1$ and $X_2$ are each independently selected from the group consisting of H, a halogen selected from the group consisting of I, Br, Cl and F, a $C_{1-4}$ alkoxy, a $C_{1-4}$ alkyl, a $C_{1-4}$ fluoroalkyl, a $C_{1-4}$ fluoroalkoxy, $CF_3$, $OCF_3$, $SCH_3$, $SCF_3$, and $NH_2$. In some embodiments, m can be 2. In some embodiments, m can be 3. In some embodiments, m can be 4. In some embodiments, m can be 5 In some embodiments, n can be 1. In some embodiments, n can be 2. In some embodiments, n can be 3. In some embodiments, n can be 4. In some embodiments, n can be 5. In some embodiments, n can be 6. In some embodiments, $X_1$ can be H. In some embodiments, $X_1$ can be methoxy ($OCH_3$). In some embodiment, $X_2$ can be methyl ($CH_3$). In some embodiment, $X_2$ can be a halogen selected from F, Cl, Br, and I. In some embodiments, $X_2$ can be bromine (Br). In some embodiments, $X_2$ can be iodine (I). In some embodiments, m=2 or 3, n=4, $X_1$=H or $OCH_3$, and $X_2$=$CH_3$, Br or I. In various embodiments, an I can be a $^{123}I$ or a $^{124}I$.

In some embodiments, a compound or salt thereof of the present teachings can include at least one $^{18}F$ isotope. A compound or a salt thereof of these embodiments can be a pegylated radiolabelled fluoroalkoxybenzamide compound or a salt thereof having a structure wherein m is an integer from 2 to 5, n is an integer from 1 to about 10, and $X_1$ and $X_2$ are each independently selected from the group consisting of H, a halogen selected from the group consisting of I, Br, Cl and F, a $C_{1-4}$ alkoxy, a $C_{1-4}$ alkyl, a $C_{1-4}$ fluoroalkyl, a $C_{1-4}$ fluoroalkoxy, $CF_3$, $OCF_3$, $SCH_3$, $SCF_3$, and $NH_2$. In some embodiments, m can be 2. In some embodiments, m can be 3. In some embodiments, m can be 4. In some embodiments, m can be 5 In some embodiments, n can be 1. In some embodiments, n can be 2. In some embodiments, n can be 3. In some embodiments, n can be 4. In some embodiments, n can be 5. In some embodiments, n can be 6. In some embodiments, $X_1$ can be H. In some embodiments, $X_1$ can be methoxy ($OCH_3$). In some embodiment, $X_2$ can be methyl ($CH_3$). In some embodiment, $X_2$ can be a halogen selected from the group consisting of F, Cl, Br, and I. In some embodiments, $X_2$ can be bromine (Br). In some embodiments, $X_2$ can be iodine (I). In some embodiments, m=2 or 3, n=4, $X_1$=H or $OCH_3$, and $X_2$=$CH_3$, Br or I.

In some embodiments, a compound or salt thereof can have a structure selected from the group consisting of (6a)

a salt thereof, (6b)

a salt thereof, (6c)

a salt thereof, (6d)

a salt thereof,

(6e)

a salt thereof,

(6f)

a salt thereof, (6g)

a salt thereof, (6h)

and a salt thereof. In some embodiments, the fluorine atom comprised by any of these compounds or salts can be an $^{18}F$. In some embodiments, in compounds or salts thereof comprising bromine, such as 6c, 6d, 6g or 6h, the bromine can be a $^{76}Br$. In some embodiments, in compounds or salts thereof comprising iodine, such as 6e or 6f, the iodine can be an $^{123}I$, an $^{124}I$ or an $^{131}I$.

Other embodiments of the present teachings include methods of synthesizing a pegylated fluoroalkoxybenzamide compound or salt thereof wherein the compound has structure wherein m is an integer from 2 to 5, n is an integer from 1 to about 10, and $X_1$ and $X_2$ are each independently selected from the group consisting of H, a halogen selected from the group consisting of I, Br, Cl and F, a $C_{1-4}$ alkoxy, a $C_{1-4}$ alkyl, a $C_{1-4}$ fluoroalkyl, a $C_{1-4}$ fluoroalkoxy, $CF_3$, $OCF_3$, $SCH_3$, $SCF_3$, and $NH_2$. In some embodiments, m can be 2. In some embodiments, m can be 3. In some embodiments, m can be 4. In some embodiments, m can be 5 In some embodiments, n can be 1. In some embodiments, n can be 2. In some embodiments, n can be 3. In some embodiments, n can be 4. In some embodiments, n can be 5. In some embodiments, n can be 6. In some embodiments, $X_1$ can be H. In some embodiments, $X_1$ can be methoxy ($OCH_3$). In some embodiment, $X_2$ can be methyl ($CH_3$). In some embodiment, $X_1$ can be a halogen selected from F, Cl, Br, and I. In some embodiments, $X_2$ can be bromine (Br). In some embodiments, $X_2$ can be iodine (I). In some embodiments, m=2 or 3, n=4, $X_1$=H or $OCH_3$, and $X_2$=$CH_3$, Br or I.

Syntheses of various fluoropegylated compounds of the present teachings are outlined in scheme 1 and scheme 2. Scheme 1: Commercially-available 6,7-dimethoxy-1,2,3,4-tetrahydroisoquinoline (1) was converted into 4-(6,7-dimethoxy-3,4-dihydroisoquinolin-2(1H)-yl)butanenitrile (2) by N-alkylation with 4-bromobutanenitrile using triethylamine as base. Reduction of intermediate 2 with lithium alumina hydride in tetrahydrofuran gave 4-(6,7-dimethoxy-3,4-dihydroisoquinolin-2(1H)-yl)butan-1-amine (3) This synthetic route to compound 3 was published previously (Tu et al. Nucl Med Biol, 2005. 32(5): p. 423-430). The target fluoropegylated compounds were made using the three step sequence shown in Scheme 2. First, the substituted salicylic acids were condensed with the intermediate 3 using N,N'-Dicyclohexylcarbodiimide (DCC) as the coupling agent to give the salicylamides 4a-d. Second, O-alkylation of the phenol group in 4a-d with diethylene glycol or triethylene glycol with potassium carbonate as base afforded benzamides 5a-h. Third, the fluoropegylated benzamides prepared by treatment of 5a-h with Diethylaminosulfur trifluoride (DAST) to give the target compounds, 6a-h.

Scheme 1:

Reagents and reaction: a) $Br(CH_2)_3CN$, $Et_3N$, $CH_2Cl_2$; b) $LiAlH_4$, THF.

Scheme 2:

Reagents and reaction conditions:
a) 4-(6,7-Dimethoxy-1,2,3,4-tetrahydroisoquinolin-2-yl)butan-1-amine (3), N,N'-Dicyclohexylcarbodiimide (DCC), HOBt, CH$_2$Cl$_2$;
b) HO(CH$_2$CH$_2$O)$_m$Cl, K$_2$CO$_3$, DMF;
c) Diethylaminosulfur trifluoride (DAST), CH$_2$Cl$_2$.

The present disclosure includes the following aspects:

1. A pegylated fluoroalkoxybenzamide compound or salt thereof of structure wherein m is an integer from 2 to 5, n is an integer from 1 to 10, and $X_1$ and $X_2$ are each independently selected from the group consisting of H, a halogen selected from the group consisting of I, Br, Cl and F, a $C_{1-4}$ alkoxy, a $C_{1-4}$ alkyl, a $C_{1-4}$ fluoroalkyl, a $C_{1-4}$ fluoroalkoxy, CF$_3$, OCF$_3$, SCH$_3$, SCF$_3$, and NH$_2$.

2. A pegylated fluoroalkoxybenzamide compound or salt thereof in accordance with aspect 1, wherein m=2, n=4, $X_1$ is H, and $X_2$ is CH$_3$.

3. A pegylated fluoroalkoxybenzamide compound or salt thereof in accordance with aspect 1, wherein m=3, n=4, $X_1$ is H, and $X_2$ is CH$_3$.

4. A pegylated fluoroalkoxybenzamide compound or salt thereof in accordance with aspect 1, wherein m=2, n=4, $X_1$ is H, and $X_2$ is Br.

5. A pegylated fluoroalkoxybenzamide compound or salt thereof in accordance with aspect 1, wherein m=3, n=4, $X_1$ is H, and $X_2$ is Br.

6. A pegylated fluoroalkoxybenzamide compound or salt thereof in accordance with aspect 1, wherein m=2, n=4, $X_1$ is H, and $X_2$ is I.

7. A pegylated fluoroalkoxybenzamide compound or salt thereof in accordance with aspect 1, wherein m=3, n=4, $X_1$ is H, and $X_2$ is I.

8. A pegylated fluoroalkoxybenzamide compound or salt thereof in accordance with aspect 1, wherein m=2, n=4, $X_1$ is methoxy, and $X_2$ is Br.

9. A pegylated fluoroalkoxybenzamide compound or salt thereof in accordance with aspect 1, wherein m=3, n=4, $X_1$ is methoxy, and $X_2$ is Br.

10. A radiolabeled pegylated fluoroalkoxybenzamide compound or salt thereof of structure wherein m is an integer from 2 to 5, n is an integer from 1 to 10, and $X_1$ and $X_2$ are each independently selected from the group consisting of H, a halogen selected from the group consisting of I, Br, Cl and F, a $C_{1-4}$ alkoxy, a $C_{1-4}$ alkyl, a $C_{1-4}$ fluoroalkyl, a $C_{1-4}$ fluoroalkoxy, $CF_3$, $OCF_3$, $SCH_3$, $SCF_3$, and $NH_2$.

11. A radiolabeled pegylated fluoroalkoxybenzamide compound or salt thereof in accordance with aspect 10, wherein m=2, n=4, $X_1$ is H, and $X_2$ is $CH_3$.

12. A radiolabeled pegylated fluoroalkoxybenzamide compound or salt thereof in accordance with aspect 10, wherein m=3, n=4, $X_1$ is H, and $X_2$ is $CH_3$.

13. A radiolabeled pegylated fluoroalkoxybenzamide compound or salt thereof in accordance with aspect 10, wherein m=2, n=4, $X_1$ is H, and $X_2$ is Br.

14. A radiolabeled pegylated fluoroalkoxybenzamide compound or salt thereof in accordance with aspect 10, wherein m=3, n=4, $X_1$ is H, and $X_2$ is Br.

15. A radiolabeled pegylated fluoroalkoxybenzamide compound or salt thereof in accordance with aspect 10, wherein m=2, n=4, $X_1$ is H, and $X_2$ is I.

16. A radiolabeled pegylated fluoroalkoxybenzamide compound or salt thereof in accordance with aspect 10, wherein m=3, n=4, $X_1$ is H, and $X_2$ is I.

17. A radiolabeled pegylated fluoroalkoxybenzamide compound or salt thereof in accordance with aspect 10, wherein m=2, n=4, $X_1$ is methoxy, and $X_2$ is Br.

18. A radiolabeled pegylated fluoroalkoxybenzamide compound or salt thereof in accordance with aspect 10, wherein m=3, n=4, $X_1$ is methoxy, and $X_2$ is Br.

19. A radiolabeled pegylated fluoroalkoxybenzamide compound or salt thereof of structure wherein m is an integer from 2 to 5, n is an integer from 1 to about 10, and $X_1$ is selected from the group consisting of H, a halogen selected from the group consisting of I, Br, Cl and F, a $C_{1-4}$ alkoxy, a $C_{1-4}$ alkyl, a $C_{1-4}$ fluoroalkyl, a $C_{1-4}$ fluoroalkoxy, $CF_3$, $OCF_3$, $SCH_3$, $SCF_3$, and $NH_2$ and $X_2$ is selected from the group consisting of $^{76}Br$, $^{123}I$ and $^{124}I$.

20. A radiolabeled pegylated fluoroalkoxybenzamide compound or salt thereof in accordance with aspect 19, wherein m=2, n=4, $X_1$ is H, and $X_2$ is $^{76}Br$.

21. A radiolabeled pegylated fluoroalkoxybenzamide compound or salt thereof in accordance with aspect 19, wherein m=3, n=4, $X_1$ is H, and $X_2$ is $^{76}Br$.

22. A radiolabeled pegylated fluoroalkoxybenzamide compound or salt thereof in accordance with aspect 19, wherein m=2, n=4, $X_1$ is H, and $X_2$ is $^{123}I$ or $^{124}I$.

23. A radiolabeled pegylated fluoroalkoxybenzamide compound or salt thereof in accordance with aspect 19, wherein m=3, n=4, $X_1$ is H, and $X_2$ is $^{123}I$ or $^{124}I$.

24. A radiolabeled pegylated fluoroalkoxybenzamide compound or salt thereof in accordance with aspect 19, wherein m=2, n=4, $X_1$ is methoxy, and $X_2$ is $^{76}Br$.

25. A radiolabeled pegylated fluoroalkoxybenzamide compound or salt thereof in accordance with aspect 19, wherein m=3, n=4, $X_1$ is methoxy, and $X_2$ is $^{76}Br$.

26. A method of imaging a tumor in a mammal, the method comprising:
administering to the mammal a radiolabelled fluoroalkoxybenzamide compound comprising a positron-emitting radionuclide of any one of aspects 10-25, or a salt thereof; and
subjecting the mammal to positron emission tomography (PET) scanning, wherein the compound comprises a positron-emitting radionuclide.

27 A method of imaging a tumor in a mammal, the method comprising:
administering to the mammal a radiolabelled fluoroalkoxybenzamide compound of any one of aspects 10-25, or a salt thereof; and
subjecting the mammal to single photon emission computed tomography (SPECT) scanning, wherein the compound comprises a gamma-emitting radionuclide.

DETAILED DESCRIPTION

The present inventors have developed a series of pegylated compounds which can be used as radiolabels for diagnostic imaging, in particular positron emission tomography (PET) imaging of tumors. The compounds selectively bind Sigma receptors, and in particular bind Sigma-2 receptors in preference to Sigma-1 receptors. The compounds are also believed to bind selectively to tumor cells, and thus can be used as tracers for detecting tumor cells. Without being limited by theory, it is generally believed that many types of tumor cells have a high density of sigma-2 receptors, and therefore compounds of the present teachings can be effective tracers for detecting tumors by virtue of the compounds' affinity for the sigma-2 receptors. In addition, because in some embodiments, the compounds comprise the radioisotope $^{18}F$, a preferred isotope for imaging by positron emission tomography (PET), they can be effective as radiotracers for PET imaging of tumors in humans or other mammals. Furthermore, in some embodiments, the compounds can comprise the gamma-emitting radioisotope $^{123}I$, a preferred isotope for imaging by single photon emission computed tomography (SPECT). These compounds can be effective as radiotracers for SPECT imaging of tumors in humans or other mammals.

The following non-limiting examples are provided to further illustrate the present teachings and are not intended to limit the scope of any claim. Unless specifically presented in the past tense, an example can be a prophetic or an actual example. The examples are not intended to limit the scope of the aspects. The methods described herein utilize laboratory techniques well known to skilled artisans, and guidance can be found in laboratory manuals and textbooks such as Sambrook, J., et al., Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; and Harlow, E., Using Antibodies: A Laboratory Manual, Cold Spring Harbor Laboratory Press, Cold Spring Harbor, N.Y., 1999; Hedrickson et al., Organic Chemistry 3rd edition, McGraw Hill, New York, 1970; Carruthers, W., and Coldham, L, Modern Methods of Organic Synthesis (4th Edition), Cambridge University Press, Cambridge, U.K., 2004; Curati, W. L., Imaging in Oncology, Cambridge University Press, Cambridge, U.K., 1998; Welch, M. J., and Redvanly, C. S., eds. Handbook of Radiopharmaceuticals: Radiochemistry and Applications, J. Wiley, New York, 2003.

In the experiments described in herein, all reagents were purchased from commercial suppliers and used without further purification unless otherwise stated. Synthetic intermediates were purchased from Aldrich Chemical Co. (Milwaukee, Wis.) and Lancaster Synthesis (Windham, Mass.) and used as received unless otherwise stated. Tetrahydrofuran (THF) was distilled from sodium hydride immediately prior to use. Anhydrous toluene was distilled from sodium/toluene shortly before use. All anhydrous and all air-sensitive reactions were carried out in oven-dried glassware under an inert nitrogen atmosphere unless otherwise stated. Standard handling techniques for air sensitive materials were employed throughout this study. When the reactions involve extraction with dichloromethane ($CH_2Cl_2$), chloroform ($CHCl_3$), ethyl acetate (EtOAc), or ethyl ether ($Et_2O$), the organic solutions was dried with anhydrous $Na_2SO_4$ and concentrated with a rotary evaporator under reduced pressure. Flash column chromatography can be conducted using silica gel 60a, "40 Micron Flash" [32-63 μm] (Scientific Adsorbents, Inc.). Melting points can be determined using the MEL-TEMP 3.0 apparatus and left uncorrected. $^1$H NMR spectra can be recorded at 300 MHz on a Varian Mercury-VX spectrometer with $CDCl_3$ as solvent and tetramethylsilane (TMS) as the internal standard. All chemical shift values are reported in ppm. Elemental analyses (C, H, N) can be determined by Atlantic Microlab, Inc. Yields were not optimized. Melting points were determined on a Haake-Buchler or MeI-Temp melting point apparatus and are uncorrected. $^1$H NMR spectra were recorded at 300 MHz on a Varian Mercury-VX spectrometer with $CDCl_3$ as the solvent and tetramethylsilane (TMS) as the internal standard. NMR spectra are referenced to the deuterium lock frequency of the spectrometer. The chemical shifts (in ppm) of residual solvents were observed at 7.26 ($CHCl_3$) or 4.78 ($CD_3OH$). The following abbreviations were used to describe peak patterns wherever appropriate: b=broad, d=doublet, t=triplet, q=quartet, m=multiplet. Analytical thin layer chromatography (TLC) was performed on Analtech GHLF silica gel glass plates, and visualization was aided by UV. Elemental analyses (C, H, N) were determined by Atlantic Microlab, Inc. The purity of the target compounds was determined by elemental analysis and by HPLC methods. All pegylated compounds reported herein have a purity ≧95%.

Example 1

This example demonstrates General procedure A for synthesizing some compounds of the present teachings.

N-(4-(6,7-dimethoxy-3,4-dihydroisoquinolin-2(1H)-yl) butyl)-2-hydroxy-5-methylbenzamide (4a). A mixture of 5-methylsalicylic acid (0.691 g, 4.5 mmol), 4-(6,7-dimethoxy-3,4-dihydroisoquinolin-2(1H)-yl)butan-1-amine (1.0 g, 3.8 mmol), N,N'-Dicyclohexylcarbodiimide (DCC) (0.94 g, 4.5 mmol) and 1-Hydroxybenzotriazole hydrate (HOBOt) (0.61 g, 4.5 mmol) in dichloromethane (20 mL) was stirred overnight under an atmosphere of nitrogen. The reaction mixture was washed with saturated sodium bicarbonate solution (3×10 mL). The organic solution was dried over $Na_2SO_4$ and volatiles were removed under reduced pressure. The residue was purified by silica gel column with methanol/ ether (5/95, v/v) as the mobile phase to afford 4a as a viscous oil (1.39 g; 93%). $^1$H NMR (300 MHz, $CDCl_3$): 1.70-1.78 (m, 4H), 2.09 (s, 3H), 2.50-2.60 (m, 2H), 2.68-2.76 (m, 2H), 2.78-2.88 (m, 2H), 3.44-3.60 (m, 4H), 3.82 (s, 3H), 3.83 (s, 3H), 6.48 (s, 1H), 6.58 (s, 1H), 6.83-6.87 (d, 1H), 7.00-7.04 (m, 1H), 7.10-7.16 (m, 1H), 7.70-7.90 (s, 1H).

Example 2

5-Bromo-N-(4-(6,7-dimethoxy-3,4-dihydroisoquinolin-2 (1H)-yl)butyl)-2-hydroxybenzamide (4b). Following procedure A (see Example 1), 1.16 g (66% yield) of 4b was obtained. $^1$H NMR (300 MHz, $CDCl_3$): 1.70-1.80 (m, 4H), 2.52-2.62 (m, 2H), 2.75-2.84 (m, 4H), 3.44-3.50 (m, 2H), 3.55-3.62 (m, 2H), 3.83 (s, 6H), 5.19 (s, 1H), 6.49 (s, 1H), 6.57 (s, 1H), 6.80-6.86 (d, 1H), 7.36-7.46 (m, 2H), 8.05-8.08 (s, 1H).

Example 3

N-(4-(6,7-dimethoxy-3,4-dihydroisoquinolin-2(1H)-yl) butyl)-2-hydroxy-5-iodobenzamide (4c). Following procedure A (see Example 1), 1.34 g (69% yield) of 4c was obtained as a white solid. $^1$H NMR (300 MHz, $CDCl_3$): 1.70-1.80 (m, 4H), 2.54-2.62 (m, 2H), 2.76-2.84 (m, 4H), 3.42-3.50 (m, 2H), 3.60 (s, 2H), 3.83 (s, 6H), 5.19 (s, 1H), 6.49 (s, 1H), 6.58 (s, 1H), 6.72-6.76 (d, 1H), 7.56-7.62 (m, 2H), 8.24-8.26 (s, 1H).

Example 4

5-Bromo-N-(4-(6,7-dimethoxy-3,4-dihydroisoquinolin-2 (1H)-yl)butyl)-2-hydroxy-3-methoxybenzamide (4d). Following procedure A, 0.73 mg (22% yield) of 4d was obtained. $^1$H NMR (300 MHz, $CDCl_3$): 1.60-1.80 (m, 4H), 2.50-2.62 (m, 2H), 2.70-2.88 (m, 4H), 3.40-3.50 (m, 2H), 3.58 (s, 2H), 3.83 (s, 3H), 3.84 (s, 3H), 3.87 (s, 3H), 5.20 (s, 1H), 6.49 (s, 1H), 6.57 (s, 1H), 6.98 (s, 1H), 7.10 (s, 1H), 4 (s, 1H).

Example 5

This example demonstrates General procedure B for synthesizing some compounds of the present teachings.

N-(4-(6,7-dimethoxy-3,4-dihydroisoquinolin-2(1H)-yl) butyl)-2-(2-(2-hydroxyethoxy)ethoxy)-5-methylbenzamide (5a). The mixture of 4a (0.65 g, 1.6 mmol), 2-(2-chloroethoxy)ethanol (0.64 g, 5.1 mmol), potassium carbonate (0.71 g, 5.1 mmol) in of N,N-Dimethylformamide (DMF) (25 mL) was refluxed over night under an atmosphere of nitrogrn. The reaction mixture was cooled to room temperature and quenched with 100 mL water. The aqueous solution was extracted with ethyl acetate (3 $X_2$ 50 mL). The combined organic layer was washed with brine (3×30 mL) and dried over $Na_2SO_4$. After concentrating under reduced pressure, the residue was purified by silica gel column chromatography with methanol/dichloromethane (10/90, v/v) as the mobile phase to afford compound 5a (0.41 g; 51% yield) as a viscous yellow oil. $^1$H NMR (300 MHz, $CDCl_3$): 1.68-1.79 (m, 4H), 2.31 (s, 3H), 2.50-2.60 (m, 2H), 2.72-2.76 (m, 2H), 2.82-2.85 (m, 2H), 3.46-3.60 (m, 8H), 3.80-3.90 (m, 8H), 4.18-4.24 (m, 2H), 6.49 (s, 1H), 6.58 (s, 1H), 6.79-6.83 (d, 1H), 7.16-7.24 (m, 1H), 7.98-7.80 (m, 1H), 8.18-8.26 (s, 1H).

Example 6

N-(4-(6,7-dimethoxy-3,4-dihydroisoquinolin-2(1H)-yl) butyl)-2-(2-(2-(2-hydroxyethoxy)ethoxy)ethoxy)-5-methyl-benzamide (5b). Following procedure B (see Example 5), 390 mg (40% yield) of 5b was obtained. $^1$H NMR (300 MHz, CDCl$_3$): 1.67-1.78 (m, 4H), 2.30 (s, 3H), 2.50-2.60 (m, 2H), 2.68-2.74 (m, 2H), 2.76-2.85 (m, 2H), 3.44-3.58 (m, 6H), 3.60-3.72 (m, 6H), 3.80-3.90 (m, 8H), 4.16-4.24 (m, 2H), 6.49 (s, 1H), 6.57 (s, 1H), 6.80-6.84 (d, 1H), 7.16-7.21 (m, 1H), 7.96-7.80 (m, 1H), 8.14-8.24 (s, 1H).

Example 7

5-Bromo-N-(4-(6,7-dimethoxy-3,4-dihydroisoquinolin-2 (1H)-yl)butyl)-2-(2-(2-hydroxyethoxy)ethoxy)-benzamide (5c). Following procedure B (see Example 5), 480 mg (70% yield) of 5c was obtained. $^1$H NMR (300 MHz, CDCl$_3$): 1.70-1.80 (m, 4H), 2.53-2.68 (m, 2H), 2.70-2.78 (m, 2H), 2.80-2.88 (m, 2H), 3.44-3.58 (m, 8H), 3.80-3.90 (m, 8H), 4.20-4.24 (m, 2H), 6.50 (s, 1H), 6.59 (s, 1H), 6.79-6.82 (d, 1H), 7.47-7.51 (m, 1H), 8.10-8.18 (s, 1H), 8.30-8.32 (s, 1H).

Example 8

5-Bromo-N-(4-(6,7-dimethoxy-3,4-dihydroisoquinolin-2 (1H)-yl)butyl)-2-(2-(2-(2-hydroxyethoxy)ethoxy)-ethoxy) benzamide (5d). Following procedure B (see Example 5), 420 mg (56% yield) of 5d was obtained. $^1$H NMR (300 MHz, CDCl$_1$): 1.70-1.80 (m, 4H), 2.53-2.68 (m, 2H), 2.70-2.78 (m, 2H), 2.80-2.88 (m, 2H), 3.44-3.58 (m, 6H), 3.60-3.75 (m, 6H), 3.80-3.90 (m, 6H), 4.20-4.24 (m, 2H), 6.50 (s, 1H), 6.58 (s, 1H), 6.78-6.82 (d, 1H), 7.47-7.51 (m, 1H), 8.10-8.18 (s, 1H), 8.30-8.32 (s, 1H).

Example 9

N-(4-(6,7-dimethoxy-3,4-dihydroisoquinolin-2(1H)-yl) butyl)-2-(2-(2-hydroxyethoxy)ethoxy)-5-iodobenzamide (5e). Following procedure B (see Example 5), 360 mg (56% yield) of 5e was obtained. $^1$H NMR (300 MHz, CDCl$_3$): 1.65-1.80 (m, 4H), 2.50-2.60 (m, 2H), 2.70-2.80 (m, 2H), 2.80-2.90 (m, 2H), 3.40-3.60 (m, 8H), 3.68-3.95 (m, 8H), 4.18-4.22 (m, 2H), 6.50 (s, 1H), 6.59 (s, 1H), 6.66-6.70 (d, 1H), 7.64-7.69 (d, 1H), 8.08-8.16 (s, 1H), 8.40-8.47 (s, 1H).

Example 10

N-(4-(6,7-dimethoxy-3,4-dihydroisoquinolin-2(1H)-yl) butyl)-2-(2-(2-(2-hydroxyethoxy)ethoxy)ethoxy)-5-iodo-benzamide (5f). Following procedure B (see Example 5), 650 mg (90% yield) of 5f was obtained. $^1$H NMR (300 MHz, CDCl$_3$): 1.62-1.80 (m, 4H), 2.50-2.60 (m, 2H), 2.68-2.76 (m, 2H), 2.76-2.86 (m, 2H), 3.40-3.56 (m, 6H), 3.58-3.70 (m, 6H), 3.70-3.95 (m, 8H), 4.16-4.22 (m, 2H), 6.49 (s, 1H), 6.58 (s, 1H), 6.66-6.70 (d, 1H), 7.64-7.68 (d, 1H), 8.04-8.16 (s, 1H), 8.40-8.43 (s, 1H).

Example 11

5-Bromo-N-(4-(6,7-dimethoxy-3,4-dihydroisoquinolin-2 (1H)-yl)butyl)-3-hydroxy-2-(2-(2-hydroxyethoxy)-ethoxy) benzamide (5g). Following procedure B (see Example 5), 0.613 mg (28% yield) of 5g was obtained. $^1$H NMR spectrum (300 MHz, CDCl$_3$): 1.65-1.80 (m, 4H), 2.50-2.60 (m, 2H), 2.70-2.78 (m, 2H), 2.80-2.88 (m, 2H), 3.40-3.65 (m, 8H), 3.70-3.75 (m, 2H), 3.83 (s, 3H), 3.84 (s, 3H), 3.85 (s, 1H), 4.16-4.22 (m, 2H), 6.50 (s, 1H), 6.58 (s, 1H), 7.08-7.10 (d, 1H), 7.82-7.84 (m, 1H), 8.28-8.36 (s, 1H).

Example 12

This example demonstrates General procedure C for synthesizing some compounds of the present teachings.

N-(4-(6,7-dimethoxy-3,4-dihydroisoquinolin-2(1H)-yl) butyl)-2-(2-(2-(2-fluoroethoxy)ethoxy)-5-methylbenzamide (6a). To solution of compound 5a (0.20 g, 0.41 mmol) in dichloromethane (60 ml) was added slowly (Diethylamino) sulfur trifluoride (DAST) (0.13 g, 0.81 mmol) at 0° C. The reaction mixture was stirred overnight under an atmosphere of nitrogen and then quenched with water (30 ml). The organic layer was separated and washed with saturated sodium carbonate solution (2×15 ml) and dried over sodium sulfate. Volatile components were removed under reduced pressure. The crude product was purified by silica gel column chromatography using ether:methanol (100:20) as the mobile phase to give 6a (0.07 g; 36% yield) as a viscous colorless oil. $^1$H NMR spectrum (300 MHz, CDCl$_3$): 1.65-1.69 (m, 4H), 2.32 (s, 3H), 2.50-2.59 (m, 2H), 2.70-2.73 (m, 2H), 2.78-2.82 (m, 2H), 3.45-3.48 (m, 2H), 3.54 (s, 2H), 3.69-3.73 (m, 1H), 3.72-3.82 (m, 7H), 3.87-3.90 (m, 2H), 4.19-4.22 (m, 2H), 4.43-4.47 (m, 1H), 4.59-4.63 (m, 1H), 6.50 (s, 1H), 6.58 (s, 1H), 6.80-6.84 (d, 1H), 7.05-7.20 (m, 1H), 7.97-7.99 (m, 1H), 8.21 (s, 1H). The free base was converted into oxalic acid salt and re-crystallized in methanol and ethyl acetate solvent. Mp 89.2-89.55° C. Elemental Analysis: $C_{27}H_{37}FN_2O_5 \cdot H_2C_2O_4 \cdot 0.5H_2O$ (C, H, N). Calcd: C, 59.27; H, 6.86; N, 4.77; Found: C, 58.95; H, 6.84; N, 4.85.

Example 13

N-(4-(6,7-dimethoxy-3,4-dihydroisoquinolin-2(1H)-yl) butyl)-2-(2-(2-(2-fluoroethoxy)ethoxy)ethoxy)-5-methyl-benzamide (6b). Same as procedure C (see Example 12), 295 mg (76% yield) of 6b was obtained. $^1$H NMR (300 MHz, CDCl$_3$): 1.60-1.80 (m, 4H); 2.32 (s, 3H), 2.50-2.59 (m, 2H), 2.70-2.76 (m, 2H), 2.78-2.84 (m, 2H), 3.42-3.50 (m, 2H), 3.55 (s, 2H), 3.60-3.80 (m, 6H), 3.80-3.90 (m, 8H), 4.19-4.24 (m, 2H), 4.43-4.47 (m, 1H), 4.58-4.62 (m, 1H), 6.50 (s, 1H), 6.57 (s, 1H), 6.80-6.84 (m, 1H), 7.17-7.23 (d, 1H), 7.96-8.01 (d, 1H), 8.19 (s, 1H). The free base was converted into oxalic acid salt and its melting point is 127.7-129.0° C. Elemental Analysis: $C_{29}H_{41}FN_2O_6 \cdot H_2C_2O_4$ (C, H, N) Calcd: C, 59.80; H, 6.96; N, 4.50; Found: C, 59.54; H, 7.03; N, 4.57.

Example 14

5-Bromo-N-(4-(6,7-dimethoxy-3,4-dihydroisoquinolin-2 (1H)-yl)butyl)-2-(2-(2-fluoroethoxy)ethoxy)benzamide (6c). Same as procedure C (see Example 12), 67 mg (14% yield) of 6c was obtained as a viscous yellow oil. $^1$H NMR spectrum (300 MHz, CDCl$_3$): 1.62-1.75 (m, 4H), 2.52-2.62 (m, 2H), 2.65-2.76 (m, 2H), 2.76-2.82 (m, 2H), 3.40-3.51 (m, 2H), 3.56 (s, 2H), 3.70-3.75 (t, 1H), 3.80-3.86 (m, 7H), 3.86-3.93 (m, 1H), 4.18-4.23 (t, 2H), 4.42-4.46 (m, 1H), 4.59-4.64 (m, 1H), 6.49 (s, 1H), 6.57 (s, 1H), 6.79-6.83 (d, 1H), 7.47-7.52 (m, 1H), 8.04-8.14 (s, 1H), 8.27-8.29 (d, 1H). The free base was converted into oxalic acid salt (mp: 124.4-126.0° C.). Elemental Analysis: $C_{26}H_{34}BrFN_2O_5 \cdot H_2C_2O_4 \cdot 0.5H_2O$ (C, H, N) Calcd: C, 51.54; H, 5.72; N, 4.29; Found: C, 51.74; H, 5.71; N, 4.21.

Example 15

5-Bromo-N-(4-(6,7-dimethoxy-3,4-dihydroisoquinolin-2(1H)-yl)butyl)-2-(2-(2-(2-fluoroethoxy)ethoxy)ethoxy)benzamide (6d). Following procedure C (see Example 12), 240 mg (58% yield) of 6d was obtained as a viscous yellow oil. $^1$H NMR (300 MHz, CDCl$_3$): 1.60-1.80 (m, 4H), 2.52-2.60 (m, 2H), 2.65-2.76 (m, 2H), 2.76-2.84 (m, 2H), 3.42-3.52 (m, 2H), 3.55 (s, 2H), 3.60-3.74 (m, 6H), 3.82 (s, 3H), 3.83 (s, 3H), 3.86-3.90 (m, 2H), 4.18-4.22 (m, 2H), 4.42-4.46 (m, 1H), 4.58-4.62 (m, 1H), 6.49 (s, 1H), 6.57 (s, 1H), 6.79-6.83 (d, 1H), 7.46-7.52 (m, 1H), 8.06-8.15 (s, 1H), 8.26-8.30 (d, 1H). The free base was converted into oxalic acid salt (mp: 89.5-91.0° C.) Elemental Analysis: $C_{28}H_{38}BrFN_2O_6 \cdot H_2C_2O_4 \cdot 0.5H_2O$ (C, H, N) Calcd: C, 51.73; H, 5.93; N, 4.02; Found: C, 51.58; H, 5.89; N, 4.06.

Example 16

N-(4-(6,7-dimethoxy-3,4-dihydroisoquinolin-2(1H)-yl)butyl)-2-(2-(2-(2-fluoroethoxy)ethoxy)ethoxy)-5-iodobenzamide (6e). Following procedure C (see Example 12), 170 mg of 6e (47% yield) was obtained as viscous brown oil. $^1$H NMR (300 MHz, CDCl$_3$): 1.60-1.70 (m, 4H), 2.52-2.60 (m, 2H), 2.64-2.74 (t, 2H), 2.76-2.84 (t, 2H), 3.40-3.49 (m, 2H), 3.54 (s, 2H), 3.68-3.73 (t, 1H), 3.73-3.85 (m, 7H), 3.85-3.92 (m, 2H), 4.18-4.22 (m, 2H), 4.40-4.46 (m, 1H), 4.58-4.62 (1H), 6.49 (s, 1H), 6.57 (s, 1H), 6.66-6.72 (d, 1H), 7.64-7.70 (m, 1H), 8.00-8.10 (s, 1H), 8.44-8.46 (d, 1H). The free base was converted into oxalic acid salt (mp: 112.0-114.0° C.). Elemental Analysis results: $C_{26}H_{34}FIN_2O_5 \cdot H_2C_2O_4$ (C, H, N) Calcd: C, 48.70; H, 5.26; N, 4.06; Found: C, 48.40; H, 5.34; N, 3.92.

Example 17

N-(4-(6,7-dimethoxy-3,4-dihydroisoquinolin-2(1H)-yl)butyl)-2-(2-(2-(2-fluoroethoxy)ethoxy)ethoxy)-5-iodobenzamide (6f). Following procedure C (see Example 12), 360 mg of 6f (56% yield) was obtained as viscous brown oil. $^1$H NMR (300 MHz, CDCl$_3$): 1.60-1.75 (m, 4H), 2.48-2.60 (m, 2H), 2.70-2.72 (t, 2H), 2.77-2.82 (t, 2H), 3.40-3.49 (m, 2H), 3.53 (s, 2H), 3.60-3.76 (m, 6H), 3.82 (s, 3H), 3.83 (s, 3H), 3.85-3.89 (m, 2H), 4.17-4.23 (m, 2H), 4.41-4.45 (m, 1H), 4.57-4.61 (m, 1H), 6.49 (s, 1H), 6.57 (s, 1H), 6.67-6.72 (d, 1H), 7.62-7.68 (m, 1H), 8.02-8.12 (s, 1H), 8.43-8.45 (d, 1H). The free base was converted into oxalic acid salt (mp: 92.0-93.5° C.). Elemental Analysis: $C_{28}H_{38}FIN_2O_6 \cdot H_2C_2O_4 \cdot 0.5H_2O$ (C, H, N) Calcd: C, 48.46; H, 5.56; N, 3.77; Found: C, 48.51; H, 5.41; N, 3.78.

Example 18

5-bromo-N-(4-(6,7-dimethoxy-3,4-dihydroisoquinolin-2(1H)-yl)butyl)-2-(2-(2-fluoroethoxy)ethoxy)-3-methoxybenzamide (6g). Following procedure C (see Example 12), 360 mg (16% yield) of 6g was obtained as a viscous brown oil. $^1$H NMR (300 MHz, CDCl$_3$): 1.60-1.78 (m, 4H), 2.48-2.63 (m, 2H), 2.66-2.75 (m, 2H), 2.76-2.85 (m, 2H), 3.40-3.51 (m, 2H), 3.57 (s, 2H), 3.68-3.73 (m, 1H), 3.72-3.80 (m, 12H), 4.16-4.29 (m, 2H), 4.44-4.50 (m, 1H), 4.60-4.67 (m, 1H), 6.51 (s, 1H), 6.58 (s, 1H), 7.09-7.12 (d, 1H), 7.85-7.88 (d, 1H), 8.30-8.40 (s, 1H). The free base was converted into oxalic acid salt (mp: 116.0-118.0° C.). Elemental Analysis: $C_{27}H_{36}BrFN_2O_6 \cdot H_2C_2O_4 \cdot H_2O$ (C, H, N) Calcd: C, 50.37; H, 5.83; N, 4.05; Found: 50.58, 5.64; 4.16.

Example 19

This example illustrates synthetic steps for generating $^{18}$F-tagged compounds of the present teachings.

Example of radiosynthesis of [$^{18}$F] compounds. ~180 mCi [$^{18}$F]fluoride can be dried by azeotropic distillation using CH$_3$CN (3×1 mL) in the presence of K$_2$CO$_3$ (0.75 mg) and K$_{222}$ (5 mg) at 110° C. under a flow of N$_2$, then a solution of a compound to be radiolabeled (2.5 mg) in CH$_3$CN (400 μL) can be added. K$_{222}$ is 4,7,13,16,21,24-Hexaoxa-1,10-diazabicyclo[8.8.8]-hexacosane (Kryptofix 222®, Acros Organics N.V., Fairlawn, N.J.). The reaction mixture can be heated in an oil bath (110° C.) for 10 min [incorporation can be, e.g., 17.3±4.4% (n=10) according to radio-TLC analysis: silica, 1:1 ethyl acetate/hexanes]. The mixture can then be passed through a silica gel Sep-Pak® (Waters) and CH$_3$CN (2×1 mL) can be used to rinse the reaction vial and the Sep-Pak®. The elution can be concentrated to less than 500 μL in the presence of 1N HCl (100 μL) at 110° C. under a flow of N$_2$, then 1N HCl (500 μL) can be added. The reaction mixture can be irradiated under microwave for 30 and 25 sec with an interval of 30 sec between each irradiation, and then can be diluted in water (3 mL) for HPLC injection. An [$^{18}$F] radiolabeled compound can be purified by reversed phased HPLC using an Alltech® Platinum EPS C18 column (250×10 mm, 10μ) eluted with 15% CH$_3$CN, 85% water with 0.1% trifluoroacetic acid (TFA) at a flow rate of 4 mL/min and UV at 272 nm. The radioactivity (~8 mCi) corresponding to a [$^{18}$F] radiolabeled compound can be collected at, e.g., 17 min, and the collection fraction can be concentrated under reduced pressure to less than 0.5 mL and then diluted in water (40 mL). An [$^{18}$F] radiolabeled compound can be separated from the dilution by passing the dilution through an Oasis® HLC cartridge (Waters) and can be eluted from the cartridge with ethanol (1~2 mL). If necessary, the ethanol solution can be concentrated under a flow of N$_2$ in order to make a final dose, e.g., for animal study with <10% ethanol in saline. The total synthesis and purification time can be 120 min; decay-corrected radiochemical yield can be, e.g., 6.2±2.1%; Radiochemical purity can be >99.9% and specific activity can be, e.g., 2,160±1,660 mCi/μmol at the end of synthesis, and can be analyzed using an analytical HPLC column (Alltech® Platinum™ EPS C18 250×4.6 mm, 10μ, 20% CH$_3$CH, 80% water, 0.1% TFA, 2 mL/min, 272 nm) and determined by comparison of the integrated UV absorbance with a calibrated mass/UV absorbance curve. The identity of a [$^{18}$F] radiolabeled compound can be confirmed by the coelution of the [$^{18}$F] radiolabeled compound with a nonradioactive standard on the analytical HPLC system.

Example 20

This example illustrates synthetic steps for generating $^{18}$F-tagged compounds of the present teachings.

Example of radiosynthesis of [$^{18}$F] compounds. [$^{18}$F]fluoride (100-150 mCi) can be added to a 10-mL Pyrex screw cap tube containing 5-6 mg of Kryptofix 222® and 0.75 mg of K$_2$CO$_3$. Using HPLC grade acetonitrile (3×1.0 mL), the water can be azeotropically evaporated from this mixture at 110° C. under a stream of argon. After all of the water is removed, a solution of a precursor (1.5-2.0 mg) in DMSO (0.2 mL) can be added to the reaction vessel containing the $^{18}$F/Kryptofix mixture. A 3 mm glass bead can be added to the reaction vessel to insure a more homogeneous heat distribution when the sample is irradiated with microwaves, and the vessel can be capped firmly on a remotely operated capping station. After vortexing, the reaction mixture can be irradiated with microwaves for 30-40 sec at medium power (60 Watts) until the thin layer chromatography scanner with a 25% of methanol and 75% dichloromethane mobile phase indicates that the incorporation yield can be 40-60%.

After adding 6 mL of water and shaking, the solution can be loaded on a C-18 reverse phase Waters Oasis® cartridge (HLB-6 cc) that has previously been rinsed with a solution of 5% methanol in water (5-8 mL). The sample can then be rinsed 3 times with 6 mL water to eliminate the unreacted fluoride. The retained activity can be eluted with 5-8 mL of acetonitrile. After evaporating the acetonitrile to a volume of <0.5 mL, the sample can be loaded on a C-18 Alltech® econosil semi-preparative HPLC column (250×10 um). The product can be eluted with 29% acetonitrile and 71% 0.1M ammonium formate buffer at a flow rate of 4.5 mL/min. The retention time of the [$^{18}$F] radiolabeled compound can be ~33 min. The solution containing the [$^{18}$F] radiolabeled compound can be concentrated, resuspended in saline, and a 100 uL aliquot sent for quality control analysis before using it in the biodistribution and imaging studies. The entire procedure requires ~2 h.

Quality control analysis can be performed on an analytical HPLC system that can consist of an Alltech® econosil reversed phase C-18 column (250×4.6 mm) with a mobile phase of 35% acetonitrile and 65% 0.1 M ammonium formate buffer at pH 4.0-4.5. At a flow rate of 1.2 mL/min, the [$^{18}$F] radiolabeled compound can elute at, e.g., 13.2 min with a radiochemical purity of >99%. The labeling yield can be ~30% (decay corrected), and the specific activity can be >2000 Ci/mmol.

Example 21

This example illustrates in vitro binding studies with the compounds of the present teachings. In this example, in vitro binding studies can be conducted in order to measure the affinity of the target compounds for $\sigma_1$ and $\sigma_2$ receptors.

In these assays, pegylated sigma ligands of the present teachings can be dissolved in N,N-dimethylformamide (DMF), DMSO or ethanol, and can then be diluted in 50 mM Tris-HCl buffer containing 150 mM NaCl and 100 mM EDTA at pH 7.4 prior to performing $\sigma_1$ and $\sigma_2$ receptor binding assays Procedures for isolating the membrane homogenates and performing the $\sigma_1$ and $\sigma_2$ receptor binding assays have been described in detail previously (Xu, J., et al., Eur. J. Pharmacol. 21: 525 (1-3): 8-17, 2005). Briefly, the $\sigma_1$ receptor binding assays can be conducted in 96-well plates using guinea pig brain membrane homogenates (~300 μg protein) and ~5 nM [$^3$H](+)-pentazocine (34.9 Ci/mmol, Perkin Elmer, Boston, Mass.). The total incubation time can be 90 min at room temperature. Nonspecific binding can be determined from samples that contain 10 μM of cold haloperidol. After 90 min, the reaction can be terminated by the addition of 150 μL of ice-cold wash buffer (10 mM Tris-HCl, 150 mM NaCl, pH 7.4) using a 96 channel transfer pipette (Fisher Scientific, Pittsburgh, Pa.). The samples can be harvested and filtered rapidly through a 96-well fiber glass filter plate (Millipore, Billerica, Mass.) that has been presoaked with 100 μL of 50 mM Tris-HCl buffer at pH 8.0 for 1 h. Each filter can be washed 3 times with 200 μL of ice-cold wash buffer, and the filter can be counted in a Wallac 1450 MicroBeta liquid scintillation counter (Perkin Elmer, Boston, Mass.).

$\sigma_2$ receptor binding assays can be conducted using rat liver membrane homogenates (~300 μg protein) and ~5 nM [$^3$H] DTG (58.1 Ci/mmol, Perkin Elmer, Boston, Mass.) in the presence of 1 μM (+)-pentazocine. The incubation time can be 120 mM at room temperature. Nonspecific binding can be determined from samples that contain 10 μM of cold haloperidol. All other procedures can be identical to those described for the $\sigma_1$ receptor binding assay above.

Data from the competitive inhibition experiments can be modeled using nonlinear regression analysis to determine the concentration that inhibits 50% of the specific binding of the radioligand (IC$_{50}$ value). Competitive curves can be best fit to a one-site fit and give pseudo-Hill coefficients of 0.6-1.0. K$_i$ values can be calculated using the method of Cheng and Prusoff (Biochem. Pharmacol. 22: 3099-3108, 1973) and can be presented as the mean±1 SEM. For these calculations, one can use a K$_d$ value of 7.89 nM for [$^3$H](+)-pentazocine and guinea pig brain; for [$^3$H]DTG and rat liver, for example 30.73 nM.

TABLE 1

| # | Pegylated Compounds | |
|---|---|---|
| | Structure | Formula |
| 6a | | $C_{27}H_{37}FN_2O_5$ (488.59) |
| 6b | | $C_{29}H_{41}FN_2O_6$ (532.64) |

TABLE 1-continued

| | Pegylated Compounds | |
|---|---|---|
| # | Structure | Formula |
| 6c |  | $C_{26}H_{34}BrFN_2O_5$ (553.46) |
| 6d |  | $C_{28}H_{38}BrFN_2O_6$ (597.51) |
| 6e |  | $C_{26}H_{34}FIN_2O_5$ (600.46) |
| 6f |  | $C_{28}H_{38}FIN_2O_6$ (644.51) |
| 6g |  | $C_{27}H_{36}BrFN_2O_6$ (583.49) |

TABLE 1-continued

Pegylated Compounds

| # | Structure | Formula |
|---|---|---|
| 6h | (structure shown) | $C_{29}H_{40}BrFN_2O_7$ (627.54) |

TABLE 2

$\sigma_1$ and $\sigma_2$ binding affinities ($K_i$) and log D of pegylated ligands (structure shown)

| # | $X_1$ | $X_2$ | m | $\sigma_1$ | $\sigma_2$ | Ratio ($\sigma_1/\sigma_2$) | Log D[a] |
|---|---|---|---|---|---|---|---|
| 6a | H | $CH_3$ | 2 | 277 ± 38 | 6.75 ± 0.9 | 41 | 2.66 |
| 6b | H | $CH_3$ | 3 | 1,922 ± 238 | 10.09 ± 0.4 | 190 | 2.30 |
| 6c | H | Br | 2 | 1,043 ± 151 | 1.38 ± 0.2 | 755 | 3.49 |
| 6d | H | Br | 3 | 1,013 ± 171 | 9.80 ± 0.4 | 103 | 3.13 |
| 6e | H | I | 2 | 451 ± 56 | 6.29 ± 0.6 | 72 | 3.74 |
| 6f | H | I | 3 | 1,278 ± 51 | 7.47 ± 1.2 | 171 | 3.38 |
| 6g | $OCH_3$ | Br | 2 | 669 ± 101 | 4.67 ± 0.6 | 143 | 3.16 |
| 6h | $OCH_3$ | Br | 3 | 9097 | 33 | 276 | ND |

[a]calculated using the program ACD/log D

Example 22

This example illustrates in vivo evaluation of compounds of the present teachings. All animal experiments can be conducted in compliance with the Guidelines for the Care and Use of Research Animals established by Washington University's Animal Studies Committee. EMT-6 mouse mammary adenocarcinoma cells ($5 \times 10^5$ cells in 100 uL of phosphate-buffered saline) can be implanted subcutaneously in the scapular region of female Balb/c mice (~2-month old and 17-22 g; Charles River Laboratories). The biodistribution studies can be initiated 7-10 days after implantation when the tumor size can be ~0.2 cm$^3$ (~200 mg).

For biodistribution studies, 10-120 µCi of an [$^{18}$F]-radiolabeled pegylated compound of the present teachings in 100-150 uL of saline can be injected via the tail vein into EMT-6 tumor-bearing female Balb/c mice. Groups of at least 4 mice can be used for each time point. At 5, 30, 60, and 120 min after injection, the mice can be euthanized, and samples of blood, lung, liver, kidney, muscle, fat, heart, brain, bone and tumor can be removed, weighed and counted in a Beckman Gamma 8000 well counter. After counting, the percentage of the injected dose per gram of tissue (% ID/g) can be calculated. The tumor/organ ratios can be calculated by dividing the % ID/g of the tumor by the % ID/g of each organ.

Labeled compounds can display tumor uptake at 5 min post-injection. Tumor uptake at 1 h post-injection can remain high for each of the ligands, and can continue to remain relatively high at 2 h post-injection in comparison to that of the normal tissues, fat and muscle. This can result in acceptable tumor:normal tissue ratios for PET imaging. Also, a low bone uptake of a labeled compound, which can continue to decrease between 30 min and 1 h time points, can suggest that these compounds do not undergo a significant defluorination in vivo.

Example 23

This example illustrates specificity of binding in vivo for $\sigma_2$ receptors by pegylated compounds of the present teachings.

To demonstrate that the in vivo binding of radiolabeled compound of the present teachings can be specific for $\sigma_2$ receptors, a no-carrier-added dose of these radiotracers can be co-injected into EMT-6 tumor-bearing mice with N-(4-fluorobenzyl)piperidinyl-4-(3-bromophenyl)acetamide (YUN-143), a sigma ligand displaying a high affinity for both $\sigma_1$ and $\sigma_2$ receptors. Co-injection of YUN-143 with a pegylated compound of the present teachings can result in a decrease in the tumor:muscle and tumor:fat ratios at 1 h post-injection.

Blocking studies in tumor-bearing mice can be conducted by co-injecting 1 mg/kg of cold N-(4-fluorobenzyl)piperidinyl-4-(3-bromophenyl)acetamide (YUN-143) with a pegylated compound of the present teachings. Yun-143 has a high affinity for both $\sigma_1$ and $\sigma_2$ receptors and is routinely used for sigma receptor blocking studies (Mach, R. H., et al., Nucl Med. Biol. 28: 451-458, 2001; Bowen, W. D. et al., Eur. J. Pharmacol. 278: 257-260, 1995; Bonhaus, D. W. et al., J. Pharmacol. Exp. Ther. 267: 961, 1993. All mice can be sacrificed 60 min after injection of the radiotracer, and the tumor:organ ratios can be determined as described above.

Example 24

This example illustrates use of radioligands of the present teachings as imaging agents.

To demonstrate feasibility of using radioligands of the present teachings as PET imaging agents for determining the $\sigma_2$ receptor status of solid tumors, a CT/PET study using a compound of the present teachings in female Balb/c mice bearing EMT-6 tumors can be performed on a microPET-F220 (CTI-Concorde Microsystems Inc.) and a MicroCAT-II system (ImTek Inc.). For the microPET studies, each mouse can be injected with ~0.25 mCi of a compound of the present teachings via the tail vein and imaged 1 h later. MicroCT images can also be obtained and co-registered with the PET images to determine the exact anatomical location of the radiotracers.

EMT-6 tumors can be identified using a radioligand. Such studies could indicate that a compound of the present teachings can be an acceptable agent for detecting solid tumors and imaging their $\sigma_2$ receptor status with PET.

Example 25

This example illustrates production of [18F]Fluoride.

[$^{18}$F]Fluoride was produced in our institution by proton irradiation of enriched $^{18}$O water (95%) [reaction: $^{18}$O(p, n)$^{18}$F] using either a JSW BC-16/8 (Japan Steel Works) or a CS-15 cyclotron (Cyclotron Corp).

Example 26

Figure 2:
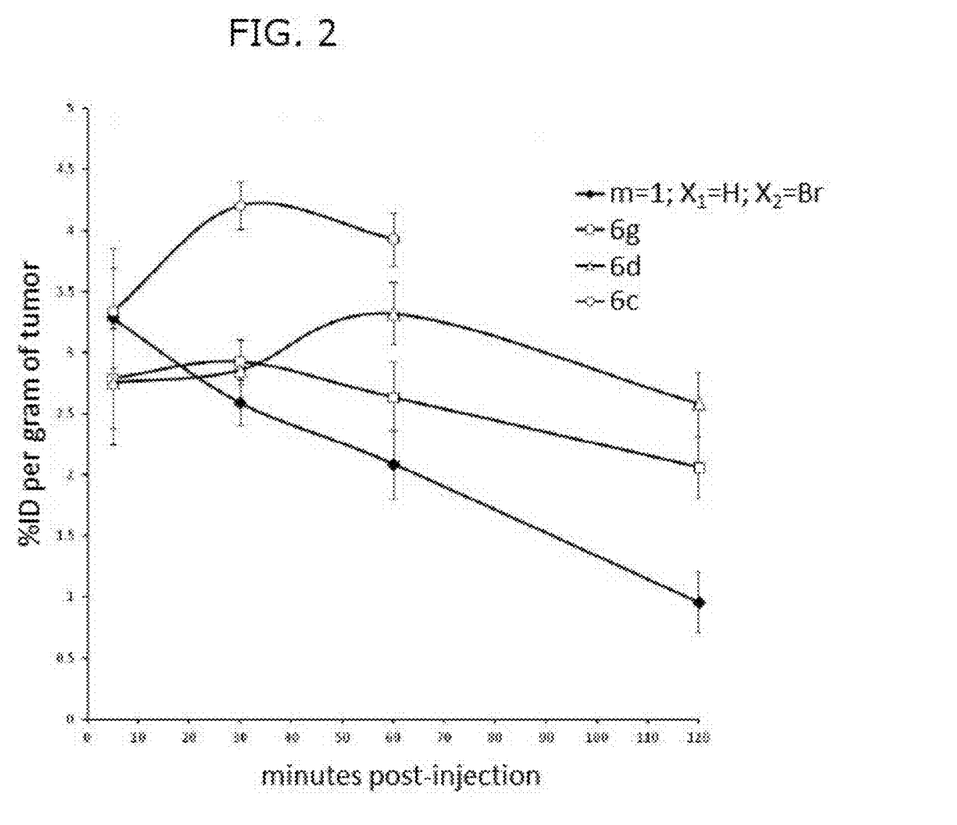
FIG. 2 illustrates tumor uptake of $^{18}F$-labeled pegylated analogs 6c, 6d and 6g versus a nonpegylated analog (m=1; $X_1$=H; $X_2$=Br).

This example illustrates tumor uptake of $^{18}$F-labeled pegylated compounds 6c, 6d and 6g versus a nonpegylated analog (m=1; $X_1$=H; $X_2$=Br).

In these experiments, various $^{18}$F-labeled pegylated compounds of the present teachings as well as a non-pegylated analog were administered to tumor-bearing mice as described in Example 22. Biodistribution of the compounds were analyzed; results are presented in FIG. 2. The pegylated compounds tested, were 6c (m=2; $X_1$=H; $X_2$=Br), 6d (m=3; $X_1$=H; $X_2$=Br) and 6g (m=2; $X_1$=OCH$_3$; $X_2$=Br). A non-pegylated analog (m=1; $X_1$=H; $X_2$=Br) was also tested. The data demonstrate higher tumor uptake compared to the non-pegylated analog. The data also demonstrate a slower rate of washout of the pegylated analogs versus the non-pegylated analog.

All patents and publications cited herein are hereby incorporated by reference, each in its entirety.

What is claimed is:

1. A radiolabeled pegylated fluoroalkoxybenzamide compound or salt thereof of structure wherein m is an integer from 2 to 5, n is an integer from 1 to 10, and $X_1$ and $X_2$ are each independently selected from the group consisting of H, a halogen selected from the group consisting of I, Br, Cl and F, a $C_{1-4}$ alkoxy, a $C_{1-4}$ alkyl, a $C_{1-4}$ fluoroalkyl, a $C_{1-4}$ fluoroalkoxy, $CF_3$, $OCF_3$, $SCH_3$, $SCF_3$, and $NH_2$.

2. A radiolabeled pegylated fluoroalkoxybenzamide compound or salt thereof in accordance with claim 1, wherein m=2, n=4, $X_1$ is H, and $X_2$ is $CH_3$.

3. A radiolabeled pegylated fluoroalkoxybenzamide compound or salt thereof in accordance with claim 1, wherein m=3, n=4, $X_1$ is H, and $X_2$ is $CH_3$.

4. A radiolabeled pegylated fluoroalkoxybenzamide compound or salt thereof in accordance with claim 1, wherein m=2, n=4, $X_1$ is H, and $X_2$ is Br.

5. A radiolabeled pegylated fluoroalkoxybenzamide compound or salt thereof in accordance with claim 1, wherein m=3, n=4, $X_1$ is H, and $X_2$ is Br.

6. A radiolabeled pegylated fluoroalkoxybenzamide compound or salt thereof in accordance with claim 1, wherein m=2, n=4, $X_1$ is H, and $X_2$ is I.

7. A radiolabeled pegylated fluoroalkoxybenzamide compound or salt thereof in accordance with claim 1, wherein m=3, n=4, $X_1$ is H, and $X_2$ is I.

8. A radiolabeled pegylated fluoroalkoxybenzamide compound or salt thereof in accordance with claim 1, wherein m=2, n=4, $X_1$ is methoxy, and $X_2$ is Br.

9. A radiolabeled pegylated fluoroalkoxybenzamide compound or salt thereof in accordance with claim 1, wherein m=3, n=4, $X_1$ is methoxy, and $X_2$ is Br.

10. A radiolabeled pegylated fluoroalkoxybenzamide compound or salt thereof of structure wherein m is an integer from 2 to 5, n is an integer from 1 to about 10, and $X_1$ is selected from the group consisting of H, a halogen selected from the group consisting of I, Br, Cl and F, a $C_{1-4}$ alkoxy, a $C_{1-4}$ alkyl, a $C_{1-4}$ fluoroalkyl, a $C_{1-4}$ fluoroalkoxy, $CF_3$, $OCF_3$, $SCH_3$, $SCF_3$, and $NH_2$ and $X_2$ is selected from the group consisting of $^{76}$Br, $^{123}$I and $^{124}$I.

11. A radiolabeled pegylated fluoroalkoxybenzamide compound or salt thereof in accordance with claim 10, wherein m=2, n=4, $X_1$ is H, and $X_2$ is $^{76}$Br.

12. A radiolabeled pegylated fluoroalkoxybenzamide compound or salt thereof in accordance with claim 10, wherein m=3, n=4, $X_1$ is H, and $X_2$ is $^{76}$Br.

13. A radiolabeled pegylated fluoroalkoxybenzamide compound or salt thereof in accordance with claim 10, wherein m=2, n=4, $X_1$ is H, and $X_2$ is $^{123}$I or $^{124}$I.

14. A radiolabeled pegylated fluoroalkoxybenzamide compound or salt thereof in accordance with claim 10, wherein m=3, n=4, $X_1$ is H, and $X_2$ is $^{123}$I or $^{124}$I.

15. A radiolabeled pegylated fluoroalkoxybenzamide compound or salt thereof in accordance with claim 10, wherein m=2, n=4, $X_1$ is methoxy, and $X_2$ is $^{76}$Br.

16. A radiolabeled pegylated fluoroalkoxybenzamide compound or salt thereof in accordance with claim 10, wherein m=3, n=4, $X_1$ is methoxy, and $X_2$ is $^{76}$Br.

17. A method of imaging a tumor in a mammal, the method comprising:
administering to the mammal a radiolabelled pegylated fluoroalkoxybenzamide compound of claim 1 or a salt thereof; and subjecting the mammal to positron emission tomography (PET) scanning.

18. A method of imaging a tumor in accordance with claim 17, wherein m=2, n=4, $X_1$ is H, and $X_2$ is Br.

19. A method of imaging a tumor in accordance with claim 17, wherein m=3, n=4, $X_1$ is methoxy, and $X_2$ is Br.

20. A method of imaging a tumor in accordance with claim 17, wherein m=3, n=4, $X_1$ is H, and $X_2$ is $CH_3$.

* * * * *